United States Patent [19]

Elango et al.

[11] Patent Number: 4,908,476

[45] Date of Patent: Mar. 13, 1990

[54] SYNTHESIS OF 2-(4-HYDROXYPHENOXY)ALKANOIC ACIDS

[75] Inventors: Varadaraj Elango; Kenneth G. Davenport, both of Corpus Christi, Tex.

[73] Assignee: Hoechst Celanese Corporation, Sommerville, N.J.

[21] Appl. No.: 170,728

[22] Filed: Mar. 21, 1988

[51] Int. Cl.$^4$ .................. C07C 69/00; C07C 59/68
[52] U.S. Cl. ...................... 560/144; 562/471
[58] Field of Search ............ 562/471; 560/144

[56] References Cited

U.S. PATENT DOCUMENTS

| | | | |
|---|---|---|---|
| 2,068,905 | 1/1937 | Bruson | 560/61 |
| 2,449,993 | 9/1948 | Gresham et al. | 562/470 |
| 3,413,341 | 11/1968 | Bursack et al. | 560/61 |
| 3,968,143 | 7/1976 | Schacht et al. | 560/61 |
| 3,976,702 | 8/1976 | Suzuki et al. | 560/61 |
| 4,035,416 | 7/1977 | Brust | 260/521 H |
| 4,051,318 | 9/1977 | Suzuki et al. | 560/131 |
| 4,130,413 | 12/1978 | Handte | 71/90 |
| 4,153,803 | 5/1979 | Thiele | 562/471 |
| 4,169,720 | 10/1979 | Schacht et al. | 71/108 |
| 4,173,709 | 11/1979 | Metivier | 562/471 |
| 4,174,460 | 11/1979 | Seifert et al. | 568/629 |
| 4,489,207 | 12/1984 | Becker et al. | 560/61 |
| 4,528,394 | 12/1985 | Otterbacher | 560/61 |
| 4,532,346 | 7/1985 | Rehn | 562/471 |
| 4,547,583 | 10/1985 | Nestler | 560/61 |
| 4,568,497 | 2/1986 | Mendoza et al. | 562/471 |
| 4,661,505 | 4/1987 | Marshall et al. | 514/381 |
| 4,665,212 | 5/1987 | Makino et al. | 560/61 |
| 4,747,865 | 5/1988 | Shiokawa . | |

FOREIGN PATENT DOCUMENTS

| | | |
|---|---|---|
| 0082413 | 6/1983 | European Pat. Off. . |
| 2003430 | 8/1969 | Fed. Rep. of Germany . |
| 55-79344 | 6/1980 | Japan . |
| 62178543 | 6/1980 | Japan . |
| 1599121 | 9/1981 | United Kingdom . |

OTHER PUBLICATIONS

Chemical Abstracts 93; 7777n, 1979.
Chemical Abstracts—77(13):88107p, 1971.
Chemical Abstracts—108(1):5692k, 1987.
Ogata, Y. (1987) J. Org. Chem, 43(12), pp. 2417–2419.
McKillop, A. (1987) Tetrahedron, 43(8), pp. 1753–1758.

*Primary Examiner*—Paul J. Killos
*Attorney, Agent, or Firm*—Donald R. Cassady

[57] ABSTRACT

A method for synthesizing 2-(4-hydroxyphenoxy)alkanoic acids by reacting a hydroxyaromatic ketone derivative with a 2-substituted alkanoic acid under basic conditions and thereafter oxidizing the intermediate with subsequent hydrolysis.

31 Claims, No Drawings

SYNTHESIS OF 2-(4-HYDROXYPHENOXY)ALKANOIC ACIDS

BACKGROUND OF THE INVENTION

The present invention relates to a method for the synthesis of 2-(4-hydroxyphenoxy)alkanoic acids. Such compounds are useful in the production of herbicides and dyes. It is known in the art to produce herbicidal agents which are of the 2-(aryloxyphenoxy)alkanoic acid class. Within this context, aryl includes phenyl, pyridyl, benzoxazolyl, etc.

These and other compounds are more fully described in U.S. Pat. Nos 4,589,908; 4,130,413; 4,391,995; 4,301,295; 4,238,626; 3,784,697; 3,721,703; 3,954,442; 4,657,577; 4,629,493; 4,046,553; and 4,368,068, all of which are incorporated herein by reference.

The production of these herbicides requires the use of an intermediate which is a 2-(4-hydroxyphenoxy)alkanoic acid or ester (I) of the formula:

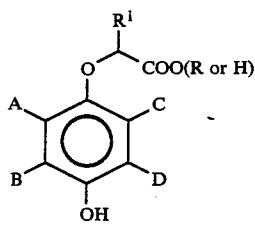

(I)

wherein the variables are hereinafter defined. However, prior processes for producing these intermediate compounds have employed hydroquinone and other compounds as starting materials. Mono-o-alkylation of hydroquinone is achieved by using a large excess of hydroquinone, but this method warrants low conversion. Alternatively, one can make mono-o-protected hydroquinone, alkylate, and remove the protecting group. However, the cost of such a manufacturing procedure is very large. Mono-o-alkylated hydroquinone derivatives, such as 2-(4-hydroxyphenoxy)propionic acid are difficult to obtain because both of the hydroxyl groups of hydroquinone tend to react with the alkylating agent. Such processes are discussed at length in U.S. Pat. Nos. 3,600,437; 4,532,346; 4,547,583; 4,613,677; 4,489,207; 4,368,068 and British Pat. No. 1,591,063. U.S. Pat. No. 4,665,212 teaches the condensation of hydroquinone or hydroquinone salts with certain aromatic sulfonyl containing acids, esters and salts. U.S. Pat. No. 4,511,731 teaches the preparation of propanoate monoethers of hydroquinone via sequential oxidation of hydroxystyrene. While such processes are effective for producing herbicide precursors, they are economically disadvantageous since the rate of conversion and selectivity, and hence the yield, is relatively low; on the order of about 10%. U.S. Pat. No. 4,528,394 describes a method which improves upon this yield by using a benzaldehyde precursor, such that the yield is increased to about 50%. However, this system is disadvantageous because of the vigorous reaction conditions required and undesired side reactions which occur such as the self-condensation of the benzaldehyde. These may also undergo undesired oxidation to carboxylic acids under Baeyer-Villiger conditions. The present invention improves on these methods by preparing intermediates derived from certain ketones and conducting a Baeyer-Villiger oxidation thereon. The intermediates are prepared in a stepwise fashion and several advantages are thereby noted. These include a higher yield, perhaps in the 80–95% range, easier purification of the intermediates and less vigorous reaction conditions.

SUMMARY OF THE INVENTION

The invention provides a method for synthesizing 2-(4-hydroxyphenoxy)alkanoic acids which comprises reacting a hydroxyaromatic ketone derivative (II) of the formula

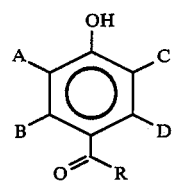

or a salt thereof; with a substituted acid of the formula

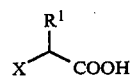

under basic conditions to thereby form a 2-(acylphenoy)alkanoic acid (III) of the formula

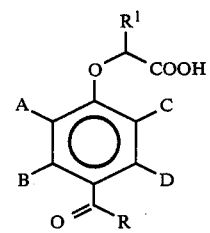

(III)

and then oxidizing the thusly formed 2-(acylphenoxy)alkanoic acid (III) with a peracid or peroxide to obtain a 2-(acyloxyphenoxy)alkanoic acid (IV) of the formula

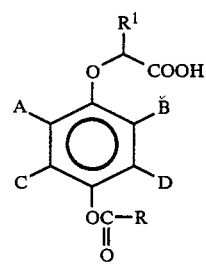

(IV)

and then hydrolyzing or alcoholizing said 2-(acyloxyphenoxy)alkanoic acid with $R^2OH/H^+$ to obtain a 2-(4-hydroxyphenoxy)alkanoic acid (V) of the formula

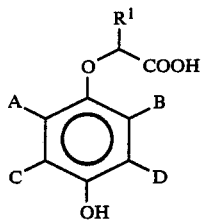 (V)

wherein R is $C_1$ to $C_{18}$ alkyl or $C_6$ to $C_{10}$ aryl, preferably $C_1$ to $C_4$ alkyl, and most preferably methyl; and wherein $R^1$ is H, phenyl or $C_1$ to $C_{18}$ alkyl, preferably $C_1$ to $C_4$ alkyl and most preferably H or methyl; and wherein $R^2$ is $C_1$ to $C_{18}$ alkyl, preferably $C_1$ to $C_4$, alkyl or aryl such as phenyl or naphthyl which may be substituted or unsubstituted; and wherein A, B, C and D are independently H, X, CN, $C_1$ to $C_{18}$ alkyl, or $C_6$ to $C_{10}$ aryl, protected using methods well-known to those skilled in the art to avoid reaction of said substituents under the conditions of the process, i.e., alkylation, oxidation, solvolysis; and X is F, Cl, Br, I or a sulfonic ester. It must however be noted that the invention is not limited to 4-substituted isomers of 2-(acylphenoxy)alkanoic acid esters but also contemplates 2- and 3-substituted 2-(acylphenoxy)alkanoic acid esters. In the alternative, instead of the aforesaid substituted acid, one could use a substituted ester of the formula:

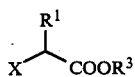

wherein $R^3$ is $C_1$ to $C_{18}$ alkyl, preferably $C_1$ to $C_4$ alkyl or aryl such as phenyl or naphthyl which may be substituted or unsubstituted. If this alternative is chosen, then an additional hydrolysis step is conducted prior to the oxidation step.

DETAILED DESCRIPTION OF THE PREFERRED EMBODIMENT

In the production of the 2-(hydroxyphenoxy)alkanoic acids (V) of this invention, one begins with a hydroxyaromatic ketone and reacts it with one of the aforesaid substituted acids under basic conditions. This reaction product is then subjected to a Baeyer-Villiger oxidation with peracetic acid being the preferred reagent. The resulting product is then hydrolyzed or alcoholized to the desired 2-(4-hydroxyphenoxy)alkanoic acids (V). The reaction sequence may be generalized as:

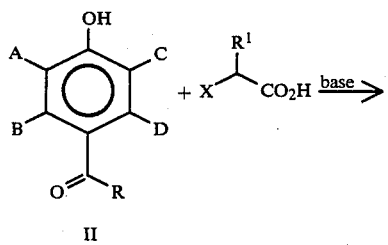

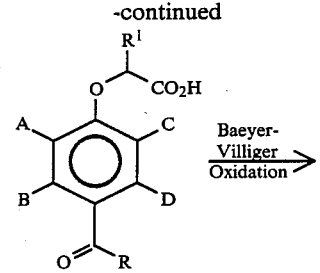

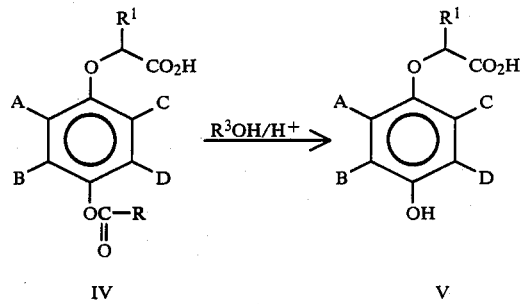

The compounds of the formulae III, IV and V possess an asymmetric carbon center and can therefore occur as pure enantiomers (optically active) or racemic as mixtures of enantiomers. An important feature of this invention is to begin the synthesis with a hydroxyaromatic ketone which is specifically a 4-hydroxyphenyl ketone compound (II). The most preferred ketone being 4-hydroxyacetophenone, as well as its sodium or potassium salts. These hydroxyaromatic ketones are then reacted with one of the aforesaid X-substituted acids which may be either racemic or optically active. Preferred acids are halogen substituted propanoic acids such as 2-chloropropanoic acid, and 2-bromopropanoic acid. This reaction proceeds by the Williamson's ether synthesis which is well-known to the skilled artisan. The reaction may take place by refluxing the hydroxyaromatic ketone with the haloalkanoic acid in a solvent such as dimethylformamide under basic conditions. The basic conditions may be provided either by direct use of a base such as an alkali metal or alkaline earth metal hydroxide or carbonate, amines or a hydride. Alternatively, within the meaning of this invention, the basic media may be provided by using one of the aforesaid salt forms of the hydroxyaromatic ketone, such as 4-hydroxyacetophenone sodium or potassium salt. Alternative solvents for the refluxing reaction non-exclusively include polar protic solvents, e.g., water or alcohol; or polar aprotic solvents, e.g., ketones, ethers, nitriles, and sulfoxides. The reaction may take place at from about 0.1 to about 72 hours, or more preferably from about 1 to about 48 hours at a temperature of from about 0° C. to about 300° C. or more preferably from about 25° C. to about 200° C.

In another embodiment of the invention, one may employ one of the aforesaid substituted esters for the substituted acids. Hydrolysis is then performed prior to the oxidation step. Suitable esters non-exclusively include halogen substituted propanoates such as methyl 2-chloropropanoate, methyl 2-bromopropanoate and ethyl 2-chloropropanoate and ethyl 2-[(methylsulfonyl)oxy]propaniate and ethyl 2-[(toluylsulfonyl)oxy]propanoate. Preferred hydrolysis agents are bases, and non-exclusively include sodium hydroxide, potassium hydroxide, and potassium carbonate.

The reaction product of this juncture is a 2-(acylphenoxy)alkanoic acid (III). In one preferred embodiment the foregoing reactants are 4-hydroxyacetophenone potassium salt and 2-bromopropanoic acid with refluxing in dimethylformamide. Alternatively, the reactants are 4-hydroxyacetophenone, potassium hydroxide and 2-bromopropanoic acid with refluxing in dimethylformamide. Therefore the preferred 2-(acylphenoxy)alkanoic acid produced is 2-(4-acetylphenoxy)propanoic acid. This is then oxidized by the Baeyer-Villiger oxidation process which is also well known to the skilled artisan per se. The oxidation is conducted by refluxing the 2-(acylphenoxy)alkanoic acid with a peracid or peroxide in a suitable solvent. The most preferred oxidizing agent is peracetic acid. Others non-exclusively include hydrogen peroxide, alkyl peroxides, chloroperacetic acid, peroxybenzoic acid, meta-chloroperoxybenzoic acid and trifluoroperoxyacetic acid. One preferred solvent for the refluxing is acetic acid. Alternative solvents for the refluxing reaction non-exclusively include water, alcohols, esters, ethers, halogenated hydrocarbons and carboxylic acids. The reaction may take place at from about 0.01 to about 24 hours, or more preferably from about 0.1 to about 10 hours at a temperature of from about 0° C. to about 100° C. or more preferably from about 25° C. to about 75° C. The reaction may be performed at either elevated or reduced pressures. However, the reaction is preferably, performed at reduced pressures to remove heat generated during the reaction. The reaction product of this juncture is a 2-(acyloxyphenoxy)alkanoic acid (IV) which in the most preferred embodiment is 2-(4-acetoxyphenoxy)propanoic acid. This latter component is then hydrolyzed or alcoholized. The alcoholysis may be conducted by contacting with alcohols under acidic conditions and elevated temperatures for a period of time sufficient to permit the reaction to approach completion. The amount of alcohol used may be, for example, about 0.5 to about 1,000 mol equivalents, preferably about 1 to about 100 mol equivalents based on the ester being alcoholized. The acids which may be employed for this purpose are organic acids such as methanesulfonic acid, para-toluenesulfonic acid, mineral acids such as sulfuric, hydrochloric and phosphoric acids, and acidic ion exchange resins. In some instances, it may be desirable to employ a combination of alcohol and water to achieve a measure of solvolysis. The alcoholysis process of this invention may also esterify the product 2-(4-hydroxyphenoxy)alkanoic acid, which in the preferred embodiment is 2-(4-hydroxyphenoxy)propanoic acid. The product of such ah esterification is alkyl 2-(4-hydroxyphenoxy)propanoate.

Alcoholysis may take place at from about 0.1 to about 10 hours, or more preferably from about 0.5 to about 4 hours at a temperature of from about 20° C. to about 200° C. or more preferably from about 60° C. to about 140° C. The reaction is conducted with an anticipated conversion of from about 90% to about 99% with a selectivity of from about 90% to about 98%. The solvolysis product is a 2-(4-hydroxyphenoxy)alkanoic acid which in the preferred embodiment is 2-(4-hydroxyphenyl)propanoic acid. The alcoholysis process of this invention provides for the recovery of the phenolic product in relatively higher yields. The product may be recovered by conventional purification methods usually involving a combination of crystallization, filtration, washing and distillation in any order deemed advantageous for the system at hand.

The following non-limiting examples serve to illustrate the invention.

EXAMPLE 1

Potassium hydroxide (17.0 g, 0.3 mol) is added to water (50 mL) and allowed to dissolve. The solution is added to 4-hydroxyacetophenone (13.6 g, 0.1 mol) to produce the potassium salt of 4-hydroxyacetophenone. 2-Bromopropanoic acid (17.0 g, 0.11 mol) is added to the potassium salt of 4-hydroxyacetophenone to give a yellow suspension. The solution is heated to reflux (102° C.) during which a yellow solution results. The solution is refluxed for 24 hours and cooled to room temperature. The pH is adjusted to 6-7 and extracted with ethyl acetate (3×100 mL) and the solution is concentrated under reduced pressure. The aqueous layer is acidified to pH 2 and extracted with ethyl acetate (3×150 mL). The solution is concentrated to give 7.0 g of a brown liquid which is 2-(4-acetylphenoxy)propanoic acid at a yield of 34%.

EXAMPLE 2

To a solution of the potassium salt of 4-hydroxyacetophenone (8.8 g, 0.05 mol) in dimethylformamide (25 mL) is added methyl 2-bromopropanoate (10.2 g, 0.06 mol) over 30 minutes and stirred at 80°-90° C. for 4 hours under nitrogen. The reaction is cooled to room temperature and methylene chloride (75 mL) and water (75 mL) are added. The organic phase is separated, washed with water (100 mL), dried and concentrated to give methyl 2-(4-acetylphenoxy)propanoate (8.5 g) (yield 76%). Methyl 2-(4-acetylphenoxy)propanoate (7.0 g, 31.5 mmol) is combined with 2N NaOH (20 mL) and refluxed overnight. Water (30 mL) is added to the reaction which is then washed with methylene chloride (50 mL). It is then acidified to pH=1 with concentrated hydrochloric acid and extracted with ethyl acetate (3×100 mL). The organic phase is dried and concentrated to provide 2-(4-acetylphenoxy)propanoic acid (5.0 g) (yield 92%): m.p. 104.3° C., IR (KBr) 3000 (br, vs), 2940 (br,s), 1754 (vs), 1650 (vs); $^1$H NMR (CDCl$_3$) delta 1.69 (d, J=6.8 Hz, 3H), 2.55 (s,3H), 4.8 (q, J=6.8 Hz, 1H), 6.92 and 7.93 (dd, J=9.0 Hz, 4H).

EXAMPLE 3

To a solution of 2-(4-acetylphenoxy)propanoic acid (5.08 g, 24.4 mmol) in acetic acid (20 mL) is added purified peracetic acid (16%, 15.80 g, 33.3 mmol) over 30 minutes. The reaction mixture is stirred under reflux at 55° C. to 60° C. and 60-64 mm Hg for 9 hours. The solution is rotovapped and vacuumed to remove the acetic acid. The product obtained is 5.0 g of 2-(4-acetoxyphenoxy)propanoic acid (yield 91%): m.p. 102° C., $^1$H NMR (CDCl$_3$, delta 1.63 (d, J=7.0 Hz, 3H), 2.26 (s, 3H), 4.85 (q, J=7.0 Hz, 1H), 7.10 (m, 4H).

EXAMPLE 4

2-(4-Acetoxyphenoxy)propanoic acid (1.2 g, 5.3 mmol) is hydrolyzed by refluxing ethanol (15 mL) and 2 drops of concentrated hydrochloric acid (36%) for 2 hours. Ethanol is removed under reduced pressure to give 2-(4-hydroxyphenoxy)propanoic acid (0.9 g yield 93%): m.p. 136°-137.5° C., IR (KBr) 3265 (vs), 1707 (vs); $^1$H NMR (acetone-d$_6$) delta 1.52 (d, J=6.8 Hz, 3H), 4.67 (q, J=6.8 Hz, 1H), 6.75 (M, 4H).

What is claimed is:

1. A method for synthesizing 2-(4-hydroxyphenoxy)alkanoic acids which comprises reacting a hydroxyaromatic ketone derivative (II) of the formula

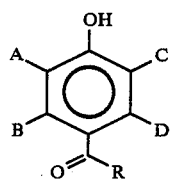

or a salt thereof; with a substituted acid of the formula

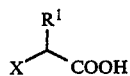

under basic conditions to thereby form a 2-(acylphenoxy)alkanoic acid (III) of the formula

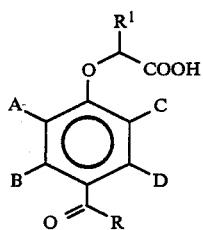

(III)

and then oxidizing the thusly formed 2-(acylphenoxy)alkanoic acid with a peracid or peroxide to obtain an 2-(ayloxyphenoxy)alkanoic acid (IV) of the formula

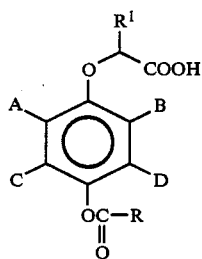

(IV)

and then hydrolyzing or transesterifying said 2-(acyloxyphenoxy)alkanoic acid with a compound of the formula $R^2OH/H^+$ to obtain a 2-(4-hydroxyphenoxy)alkanoic acid (V) of the formula

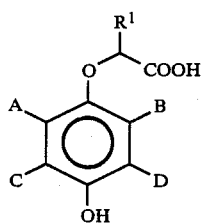

(V)

wherein R is $C_1$ to $C_{18}$ alkyl or $C_6$ to $C_{10}$ aryl; and wherein $R^1$ is H, phenyl or $C_1$ to $C_{18}$ alkyl; and wherein $R^2$ is $C_1$ to $C_{18}$ alkyl, or aryl; and wherein A, B, C and D are independently H, X, CN, $C_1$ to $C_{18}$ alkyl, or $C_6$ to $C_{10}$ aryl; and X is F, Cl, Br, I or a sulfonic ester.

2. The method of claim 1 wherein A, B, C and D are hydrogen.

3. The method of claim 1 wherein R is $CH_3$.

4. The method of claim 1 wherein said hydroxyaromatic ketone is a potassium or sodium salt.

5. The method of claim 1 wherein $R^1$ is $CH_3$.

6. The method of claim 1 wherein X is bromine, chlorine mesylate or tosylate.

7. The method of claim 1 wherein $R^1$ is $CH_3$, and X is bromine.

8. The method of claim 1 wherein said base is sodium hydroxide or potassium carbonate.

9. The method of claim 1 wherein said base is selected from the group consisting of alkali metal and alkaline earth metal hydroxides or carbonates, amines and hydrides.

10. The method of claim 1 wherein said oxidation is conducted with peracetic acid.

11. The method of claim 1 wherein oxidation is conducted with a compound selected from the group consisting of chloroperacetic acid, peroxybenzoic acid, meta-chloroperoxybenzoic acid, trifluoroperoxyacetic acid, an alkyl peroxide or hydrogen peroxide.

12. The method of claim 1 wherein said hydrolysis or alcoholysis is conducted with an alcohol, an ion exchange resin or an acid.

13. The method of claim 1 wherein said hydrolysis is conducted with hydrochloric acid.

14. The method of claim 5 wherein R is methyl.

15. The method of claim 14 wherein A, B, C and D are hydrogen.

16. The method of claim 1 wherein A, B, C and D are hydrogen, R is methyl and the oxidation is conducted with peracetic acid.

17. The method of claim 1 wherein said substituted acid is an optically active substance.

18. A method for synthesizing 2-(4-hydroxyphenoxy)alkanoic acids which comprises reacting a hydroxyaromatic ketone derivative (II) of the formula

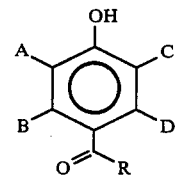

or a salt thereof; with a substituted ester of the formula

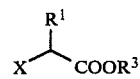

under basic conditions to thereby form a 2-(acylphenoxy)alkanoic acid ester of the formula

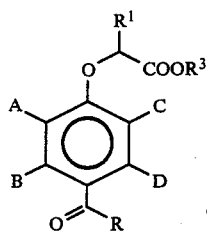

and then hydrolyzing the thusly formed 2-(acylphenoxy)alkanoic acid ester to form a 2-(acylphenoxy)alkanoic acid (III) of the formula

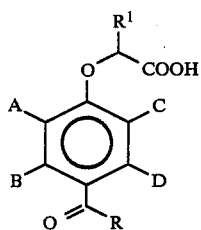

and then oxidizing the thusly formed 2-(acylphenoxy)alkanoic acid with a peracid or peroxide to obtain a 2-(acyloxyphenoxy)alkanoic acid (IV) of the formula

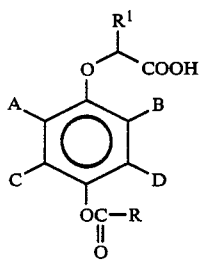

and then hydrolyzing or alcoholizing said 2-(acyloxyphenoxy)alkanoic acid with a compound of the formula $R^2H^+$ to obtain a 2-(4-hydroxyphenoxy)alkanoic acid (V) of the formula

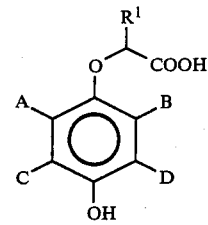

wherein R is $C_1$ to $C_{18}$ alkyl or $C_6$ to $C_{10}$ aryl; and wherein $R^1$ is H, phenyl or $C_1$ to $C_{18}$ alkyl; and wherein $R^2$ and $R^3$ are independently $C_1$ to $C_{18}$ alkyl, or aryl; and wherein A, B, C and D are independently H, X, CN, $C_1$ to $C_{18}$ alkyl, or $C_6$ to $C_{10}$ aryl; and X is F, Cl, Br, I or a sulfonic ester.

19. The method of claim 18 wherein A, B, C and D are hydrogen.

20. The method of claim 18 wherein R is $CH_3$.

21. The method of claim 18 wherein said hydroxyaromatic ketone is a potassium or sodium salt.

22. The method of claim 18 wherein $R^1$ is $CH_3$.

23. The method of claim 18 wherein X is bromine, chlorine, mesylate or tosylate.

24. The method of claim 18 wherein $R^1$ is $CH_3$, and X is bromine.

25. The method of claim 18 wherein said base is sodium hydroxide or potassium carbonate.

26. The method of claim 18 wherein said base is selected from the group consisting of alkali metal and alkaline earth metal hydroxides or carbonates, amines and hydrides.

27. The method of claim 18 wherein said oxidation is conducted with peracetic acid.

28. The method of claim 18 wherein oxidation is conducted with a compound selected from the group consisting of chloroperacetic acid, peroxybenzoic acid, meta-chloroperoxybenzoic acid, trifluoroperoxyacetic acid, an alkyl peroxide or hydrogen peroxide.

29. The method of claim 18 wherein said hydrolysis or alcoholysis steps are conducted with an alcohol, an ion exchange resin, an acid or a base.

30. The method of claim 18 wherein said X-substituted acid is an
optically active compound.

31. The compound 2-(4-acetoxyphenoxy)propanoic acid.

* * * * *

UNITED STATES PATENT AND TRADEMARK OFFICE
CERTIFICATE OF CORRECTION

PATENT NO. : 4,908,476
DATED : 3/13/90
INVENTOR(S) : V. Elango, K. G. Davenport

It is certified that error appears in the above-identified patent and that said Letters Patent is hereby corrected as shown below:

Col. 2, line 54-64, formula (IV) should read

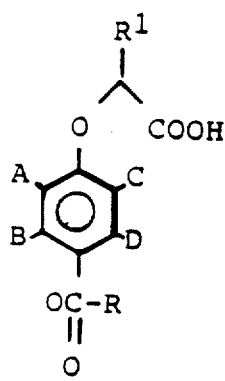

Col. 3, line 1-10, formula (V) should read

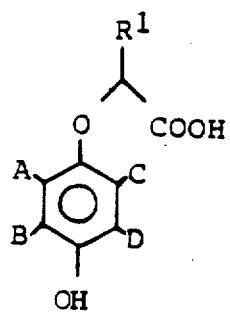

Col. 4, line 19-20, arrow formula should read

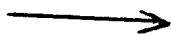

Col. 5, line 53, Delete "ah" after the word --such-- insert "an".

UNITED STATES PATENT AND TRADEMARK OFFICE
CERTIFICATE OF CORRECTION

PATENT NO. : 4,908,476

DATED : 3/13/90

INVENTOR(S) : V. Elango, K. G. Davenport

It is certified that error appears in the above-identified patent and that said Letters Patent is hereby corrected as shown below:

Col. 7, line 38-48, formula (IV) should read

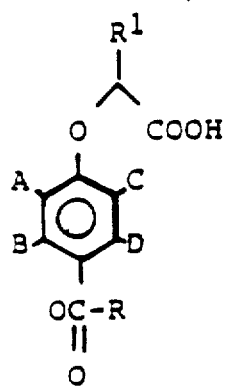

Col. 7, line 54-62, formula (V) should read

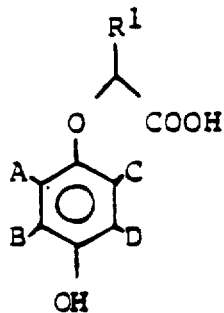

UNITED STATES PATENT AND TRADEMARK OFFICE
CERTIFICATE OF CORRECTION

PATENT NO.  : 4,908,476
DATED       : 3/13/90
INVENTOR(S) : V. Elango, K. G. Davenport It is certified that error appears in the above-identified patent and that said Letters Patent is hereby corrected as shown below:

Col. 9, line 33-43, formula (IV) should read

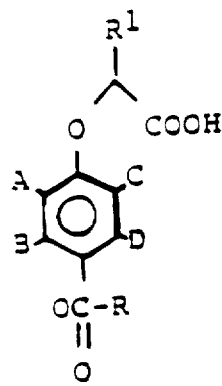

UNITED STATES PATENT AND TRADEMARK OFFICE
CERTIFICATE OF CORRECTION

PATENT NO. : 4,908,476
DATED : 3/13/90
INVENTOR(S) : V. Elango, K. G. Davenport

It is certified that error appears in the above-identified patent and that said Letters Patent is hereby corrected as shown below:

Col. 9, line 48, $R^2H^+$ should read, --$R^2OH/H^+$--

Col. 10, line 1-10, formula (V) should read

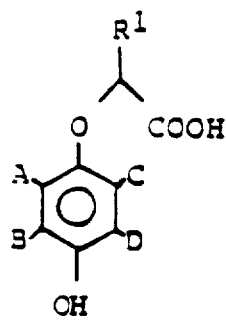

Signed and Sealed this

Thirtieth Day of June, 1992

Attest:

DOUGLAS B. COMER

*Attesting Officer*

*Acting Commissioner of Patents and Trademarks*